United States Patent
Li et al.

(10) Patent No.: US 10,537,881 B2
(45) Date of Patent: Jan. 21, 2020

(54) METHODS OF MAKING SUPPORTED NI/PT BIMETALLIC NANOPARTICLES AND NI/PT MULTILAYER CORE-SHELL STRUCTURES AND THEIR USES FOR CO2 REFORMING

(71) Applicant: KING ABDULLAH UNIVERSITY OF SCIENCE AND TECHNOLOGY, Thuwal (SA)

(72) Inventors: Lidong Li, Thuwal (SA); Dalaver H. Anjum, Thuwal (SA); Lu Zhou, Thuwal (SA); Paco Laveille, Thuwal (SA); Jean-Marie Basset, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 89 days.

(21) Appl. No.: 15/103,907

(22) PCT Filed: Dec. 17, 2014

(86) PCT No.: PCT/IB2014/003199
§ 371 (c)(1),
(2) Date: Jun. 13, 2016

(87) PCT Pub. No.: WO2015/092551
PCT Pub. Date: Jun. 25, 2015

(65) Prior Publication Data
US 2016/0318004 A1    Nov. 3, 2016

Related U.S. Application Data

(60) Provisional application No. 61/917,395, filed on Dec. 18, 2013.

(51) Int. Cl.
*B01J 23/89* (2006.01)
*B01J 37/18* (2006.01)
(Continued)

(52) U.S. Cl.
CPC ............. *B01J 23/892* (2013.01); *B01J 21/04* (2013.01); *B01J 35/002* (2013.01);
(Continued)

(58) Field of Classification Search
CPC ................................ B01J 23/892; B01L 21/04
See application file for complete search history.

(56) References Cited

U.S. PATENT DOCUMENTS

2007/0282124 A1* 12/2007 Eastham .............. B01J 31/0225
560/207
2008/0000222 A1*  1/2008 Hirata ................. B01D 53/9422
60/297
(Continued)

FOREIGN PATENT DOCUMENTS

EP          1518600 A1     3/2005
EP          2810714 A1    12/2014
(Continued)

OTHER PUBLICATIONS

Pawelec et al: "Structural and surface features of PtNi catalysts for reforming of methane with CO2", Applied Catalysis A: General. Elsevier Science. Amsterdam. NL, vol. 323, Apr. 23, 2007 (Apr. 23, 2007), pp. 188-201. XP022021811, ISSN: 0926-860X. DOI:10.1016/J.APCATA.2007.02.017.
(Continued)

*Primary Examiner* — Paul A Wartalowicz
(74) *Attorney, Agent, or Firm* — Billion & Armitage; Lisbeth C. Robinson

(57) ABSTRACT

Embodiments of the present disclosure provide for supported Ni/Pt bimetallic nanoparticles having a Ni core and a Pt layer disposed on the surface of the Ni core, compositions including supported NiPt nanoparticles, methods of making supported NiPt nanoparticles, methods of using supported NiPt nanoparticles, and the like.

9 Claims, 10 Drawing Sheets

Scheme 1 Syntheses of alumina-supported Ni/Pt core-shell NPs.

(51) Int. Cl.
*B01J 35/00* (2006.01)
*B01J 35/02* (2006.01)
*C01B 3/26* (2006.01)
*C01B 3/58* (2006.01)
*C07C 5/03* (2006.01)
*B01J 37/02* (2006.01)
*B01J 21/04* (2006.01)
*B01J 37/04* (2006.01)
*B01J 37/08* (2006.01)
*B82Y 40/00* (2011.01)
*B01J 37/16* (2006.01)
*B01J 35/10* (2006.01)
*B82Y 30/00* (2011.01)

(52) U.S. Cl.
CPC ......... *B01J 35/0006* (2013.01); *B01J 35/008* (2013.01); *B01J 35/0013* (2013.01); *B01J 35/0086* (2013.01); *B01J 35/023* (2013.01); *B01J 37/0207* (2013.01); *B01J 37/0209* (2013.01); *B01J 37/0211* (2013.01); *B01J 37/0244* (2013.01); *B01J 37/04* (2013.01); *B01J 37/08* (2013.01); *B01J 37/18* (2013.01); *C01B 3/26* (2013.01); *C01B 3/583* (2013.01); *C07C 5/03* (2013.01); *B01J 35/0066* (2013.01); *B01J 35/1019* (2013.01); *B01J 35/1038* (2013.01); *B01J 37/0248* (2013.01); *B01J 37/16* (2013.01); *B82Y 30/00* (2013.01); *B82Y 40/00* (2013.01); *C01B 2203/0238* (2013.01); *C01B 2203/0277* (2013.01); *C01B 2203/044* (2013.01); *C01B 2203/047* (2013.01); *C01B 2203/107* (2013.01); *C01B 2203/1058* (2013.01); *C01B 2203/1082* (2013.01); *C01B 2203/1241* (2013.01); *C07C 2521/04* (2013.01); *C07C 2521/06* (2013.01); *C07C 2521/08* (2013.01); *C07C 2521/18* (2013.01); *C07C 2523/42* (2013.01); *C07C 2523/755* (2013.01); *C07C 2523/89* (2013.01); *Y02P 20/52* (2015.11)

(56) References Cited

U.S. PATENT DOCUMENTS

2011/0151353 A1* 6/2011 Haug ................. H01M 4/8657
429/482
2014/0171290 A1* 6/2014 Lopez ................. B01J 23/892
502/1

FOREIGN PATENT DOCUMENTS

WO 2007015620 A1 2/2007
WO 2014058767 A1 4/2014

OTHER PUBLICATIONS

International Search Report and Written Opinion of Application No. PCT/IB2014/003199 dated Jul. 23, 2015.

* cited by examiner

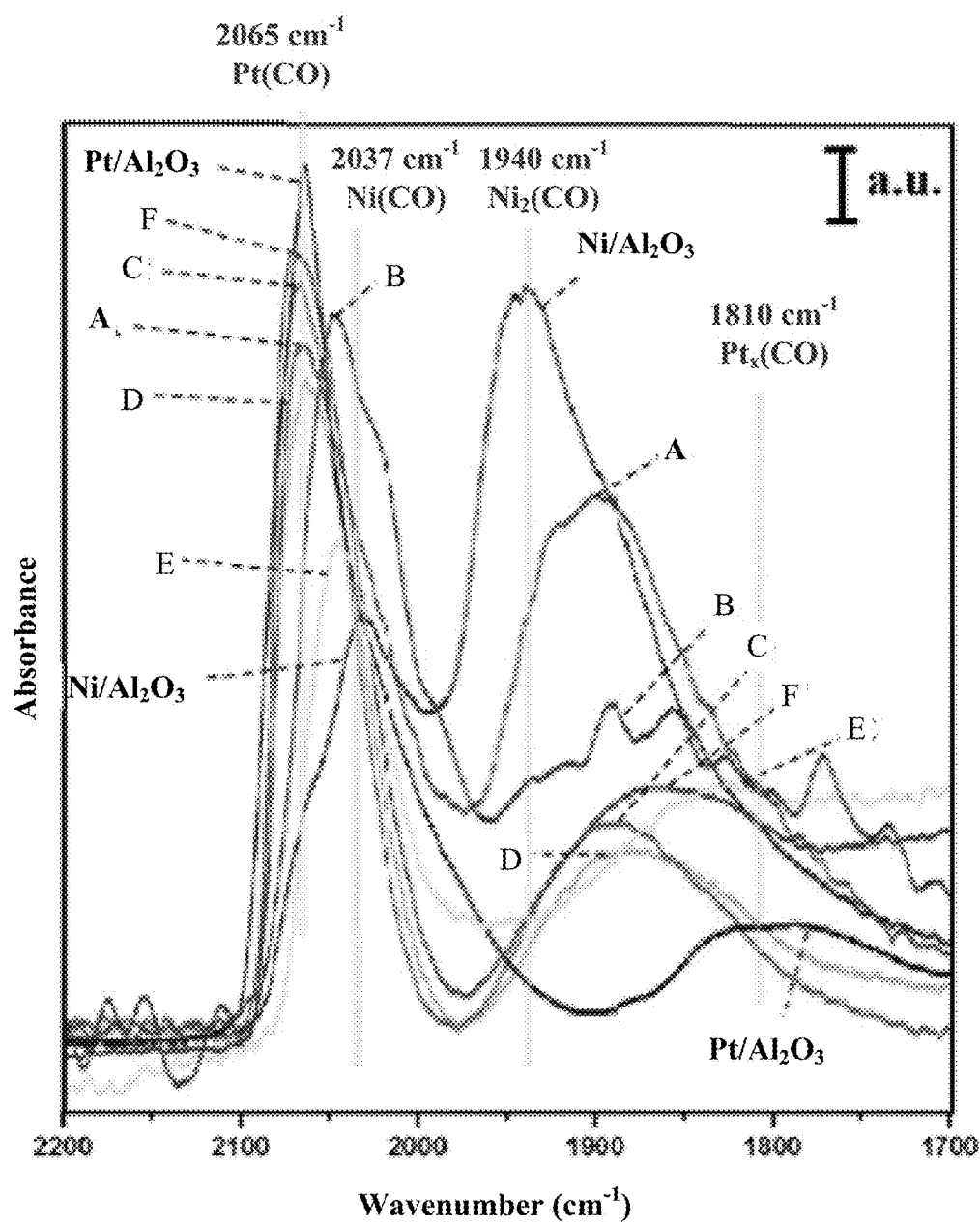
FIG. 1.1

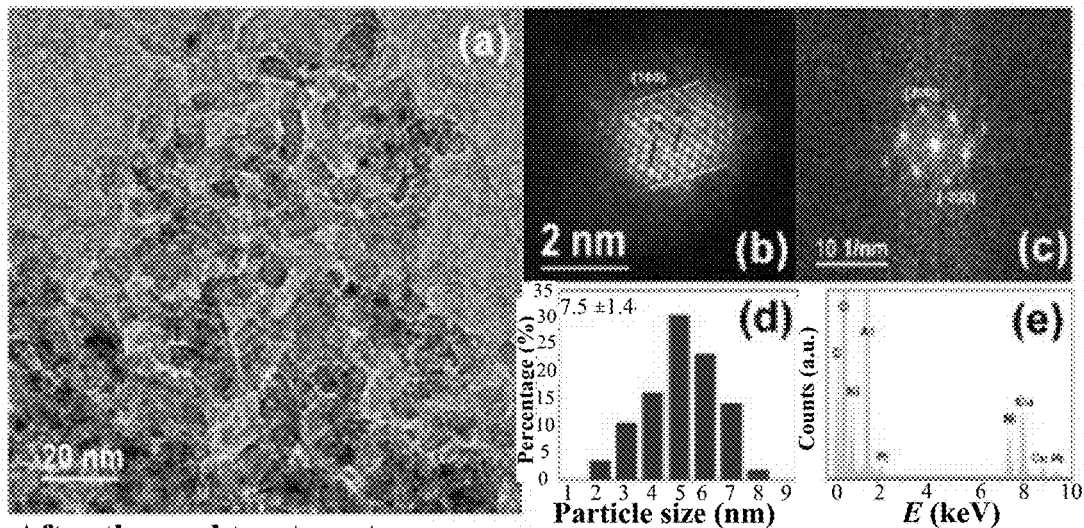
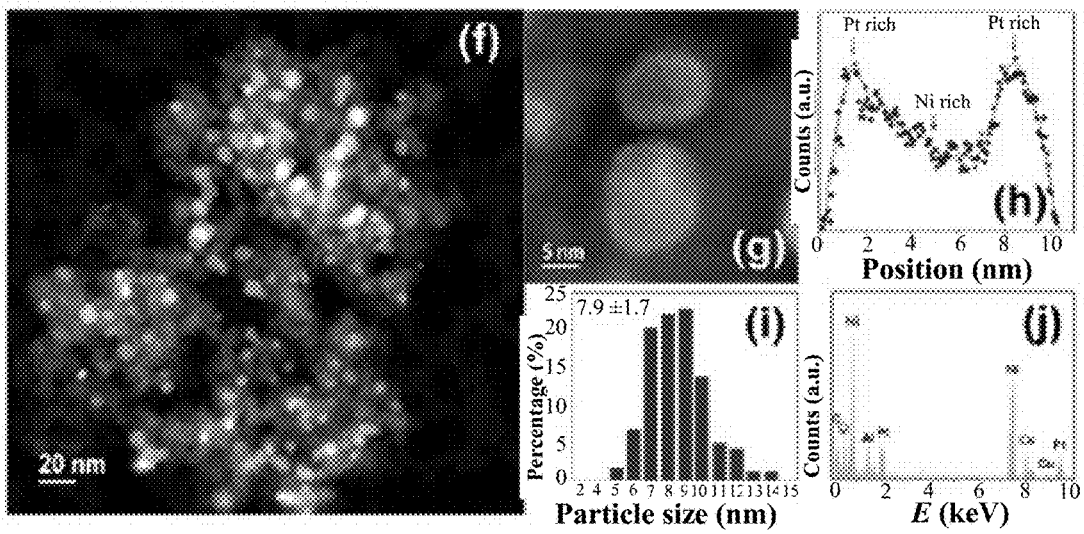
FIG. 1.2

Before thermal treatment
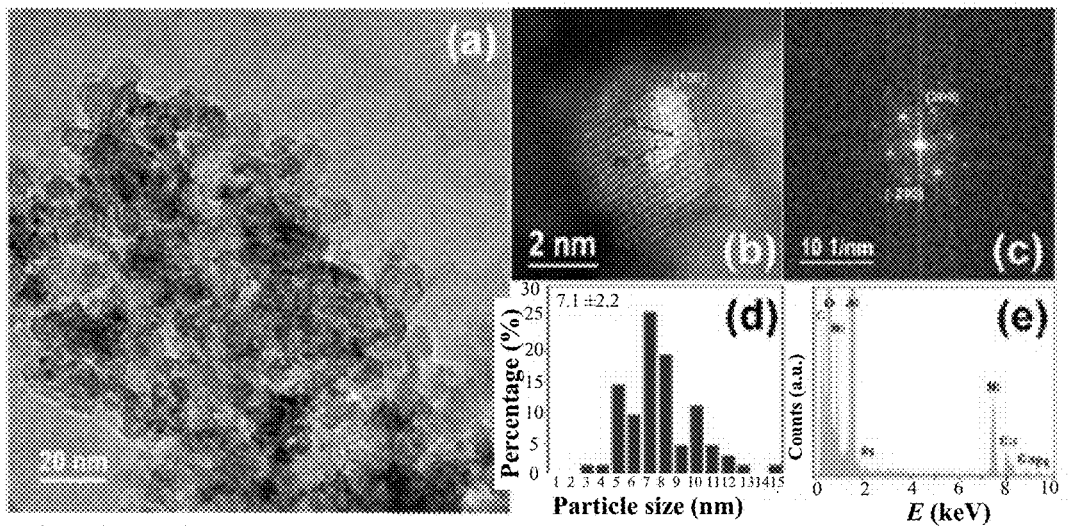
After thermal treatment
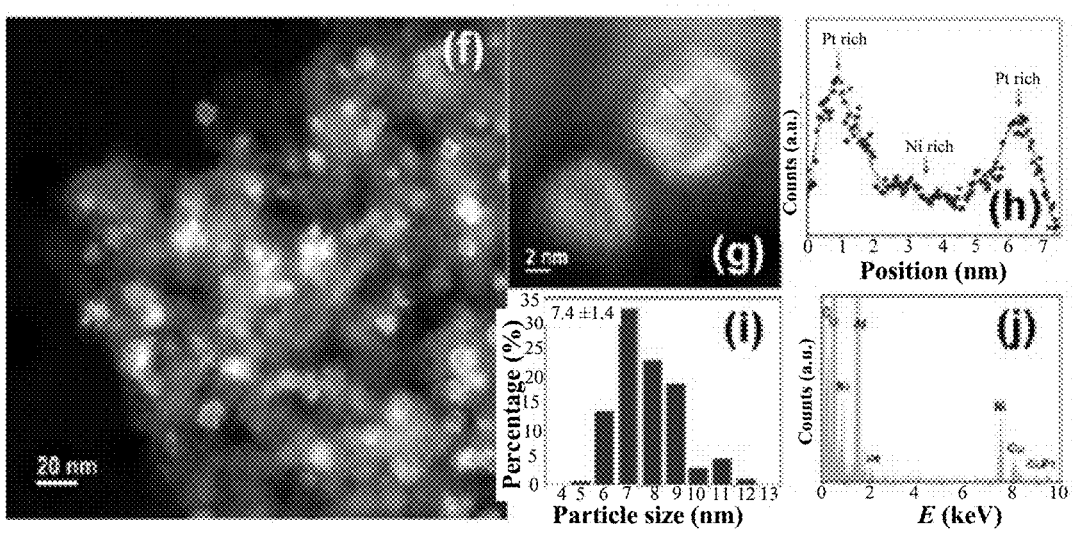
FIG. 1.3

Before thermal treatment
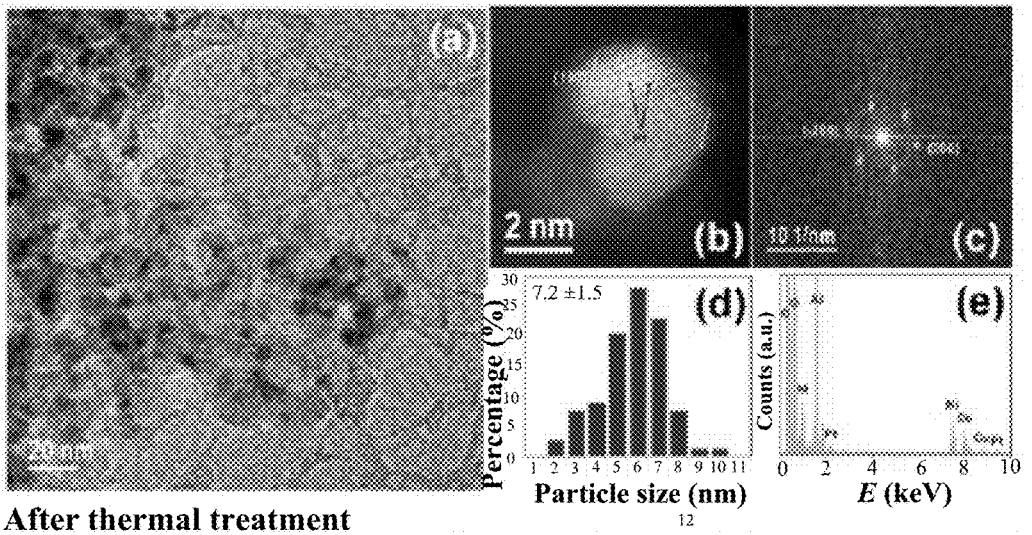
After thermal treatment
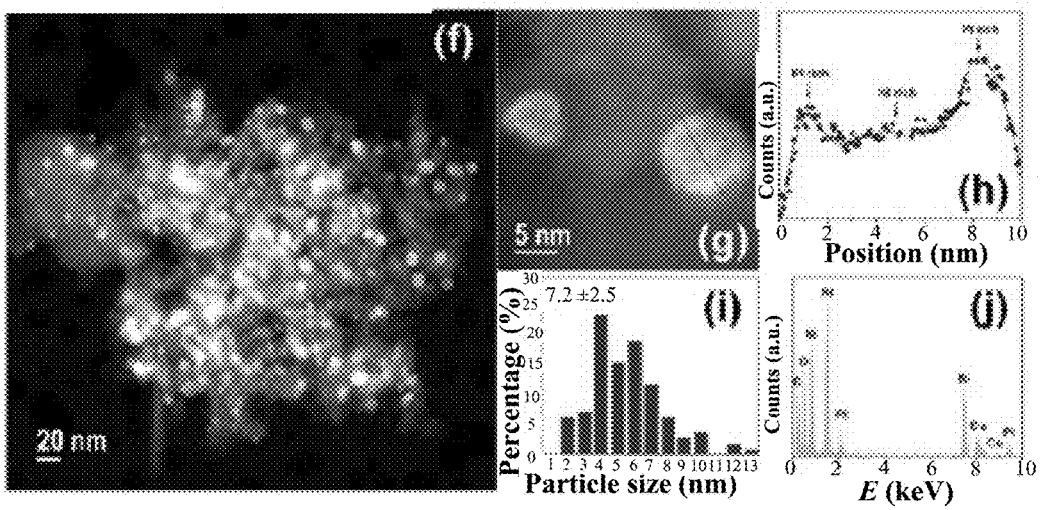
FIG. 1.4

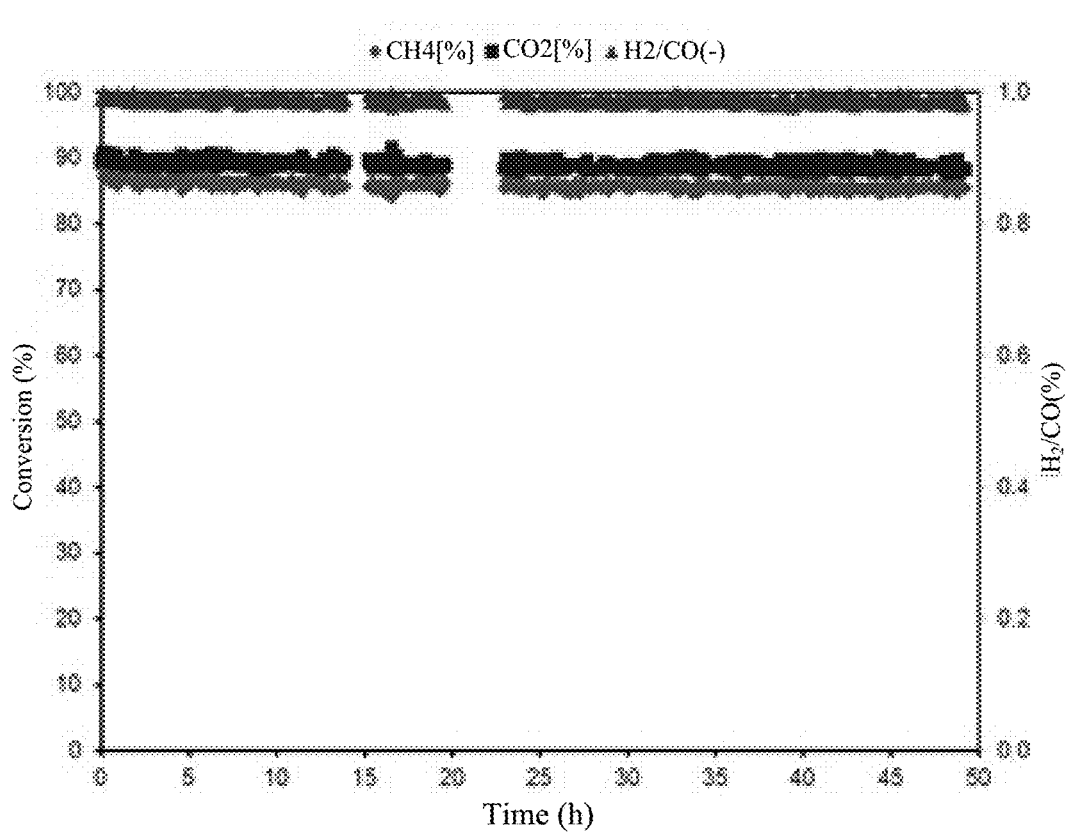
FIG. 1.5

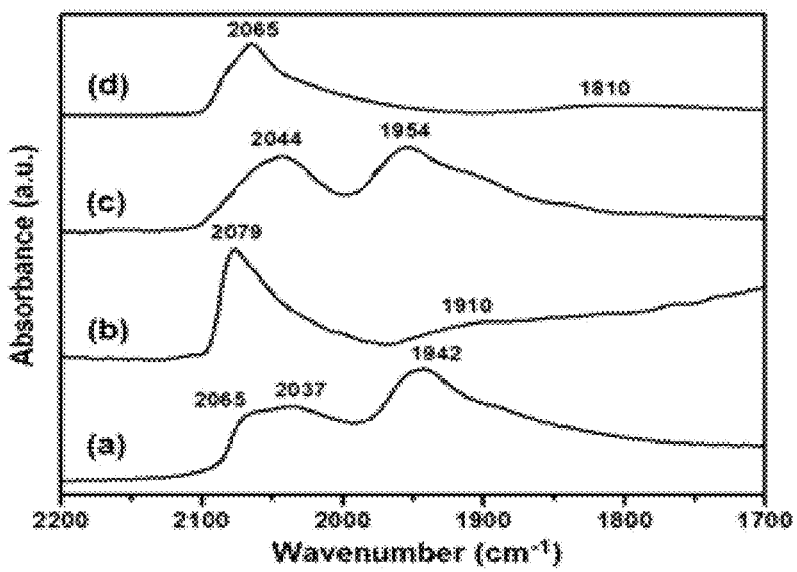
FIG. 2.1
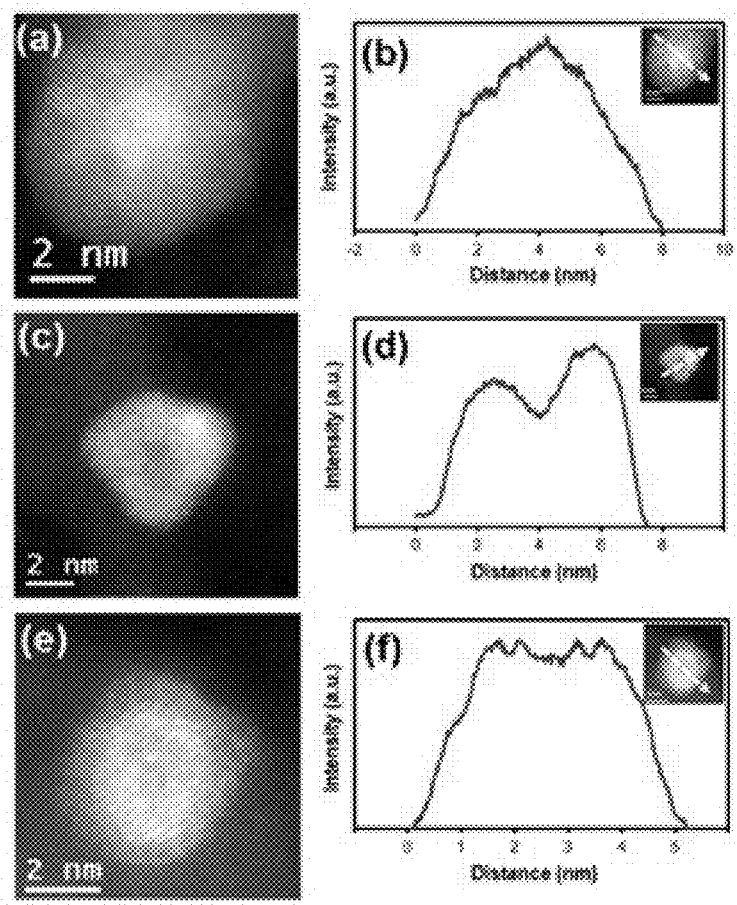
FIG. 2.2

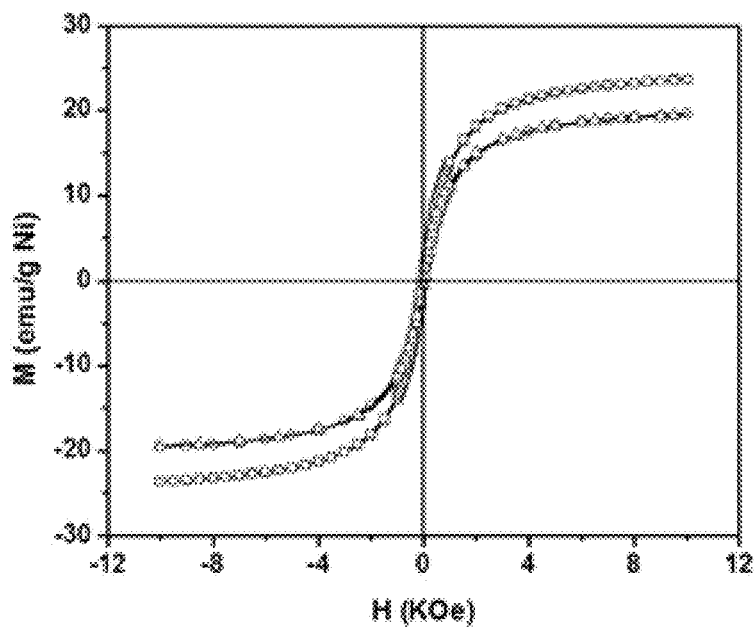
FIG. 2.3
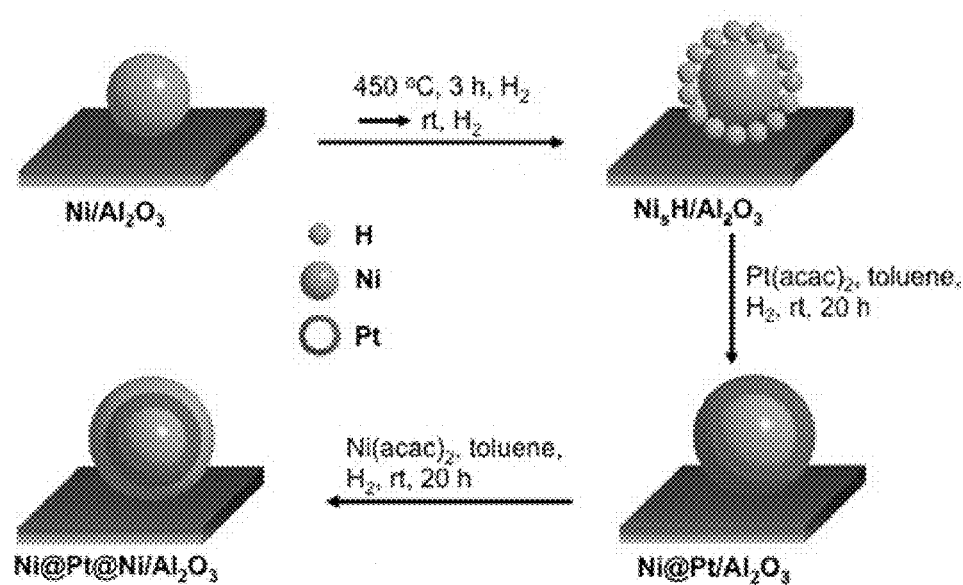
Scheme 1 Syntheses of alumina-supported Ni/Pt core-shell NPs.
FIG. 2.4

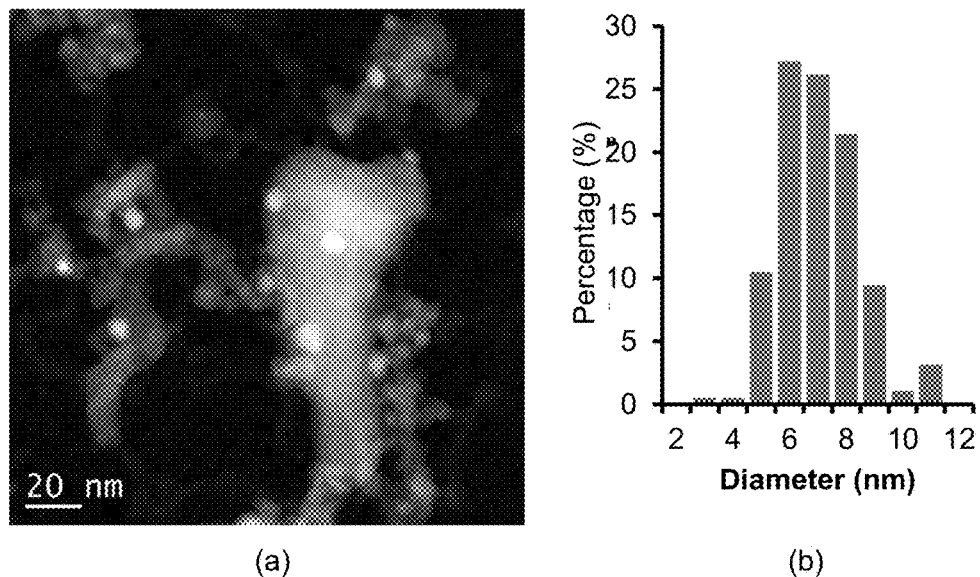
(a)  (b)
FIG. 3.1
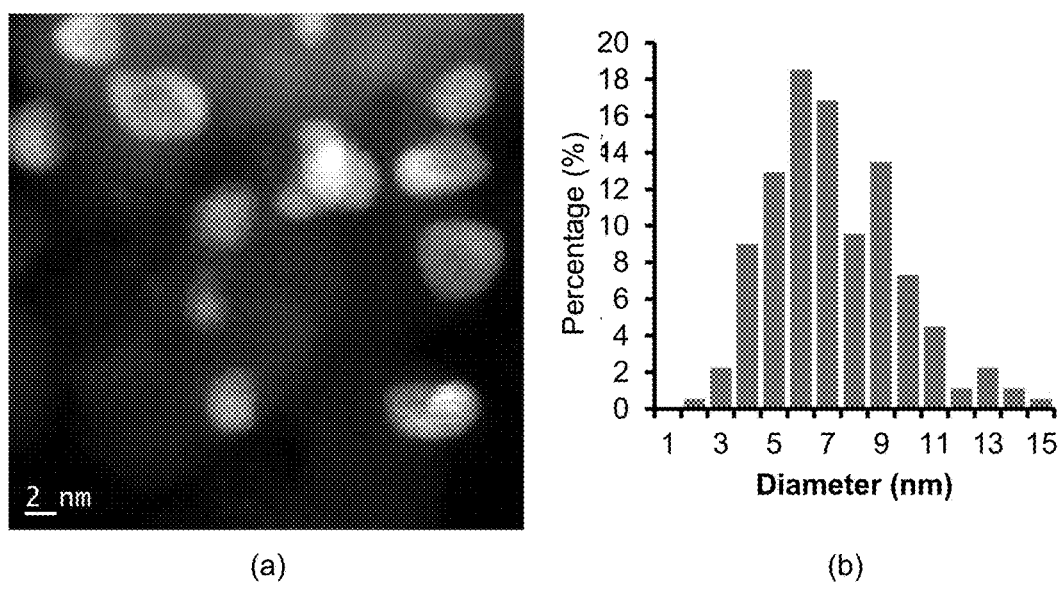
(a)  (b)
FIG. 3.2

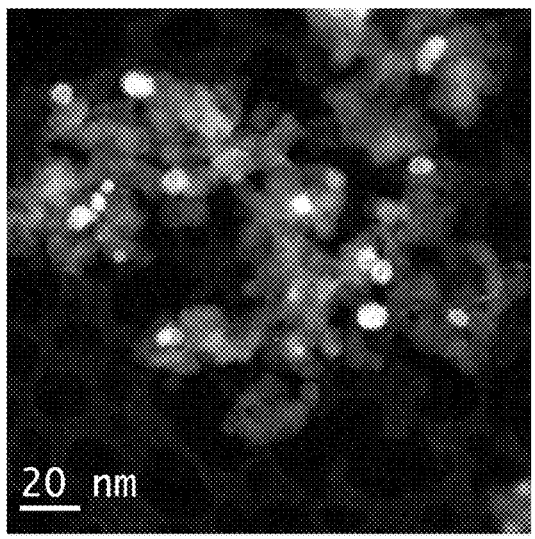 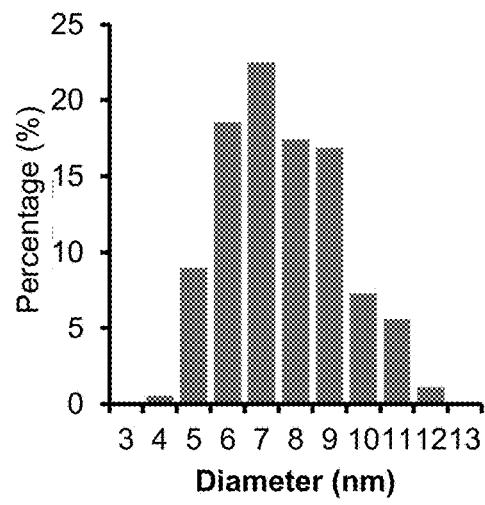
(a) (b)
FIG. 3.3
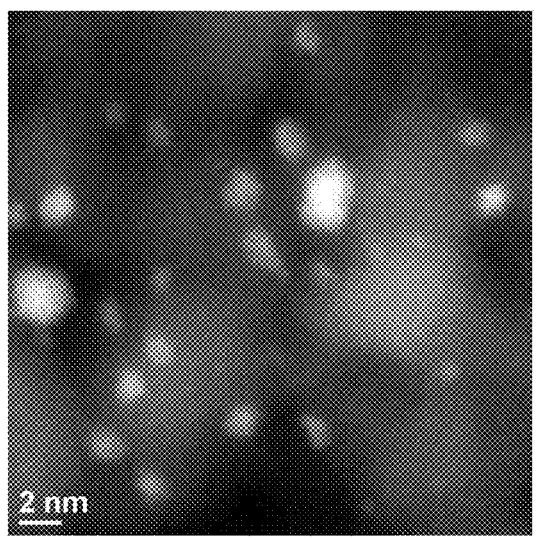 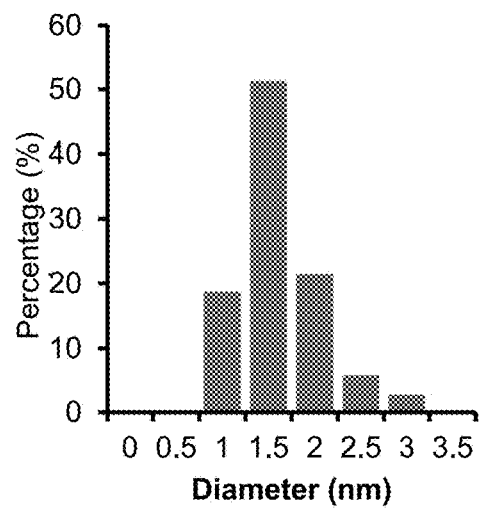
(a) (b)
FIG. 3.4

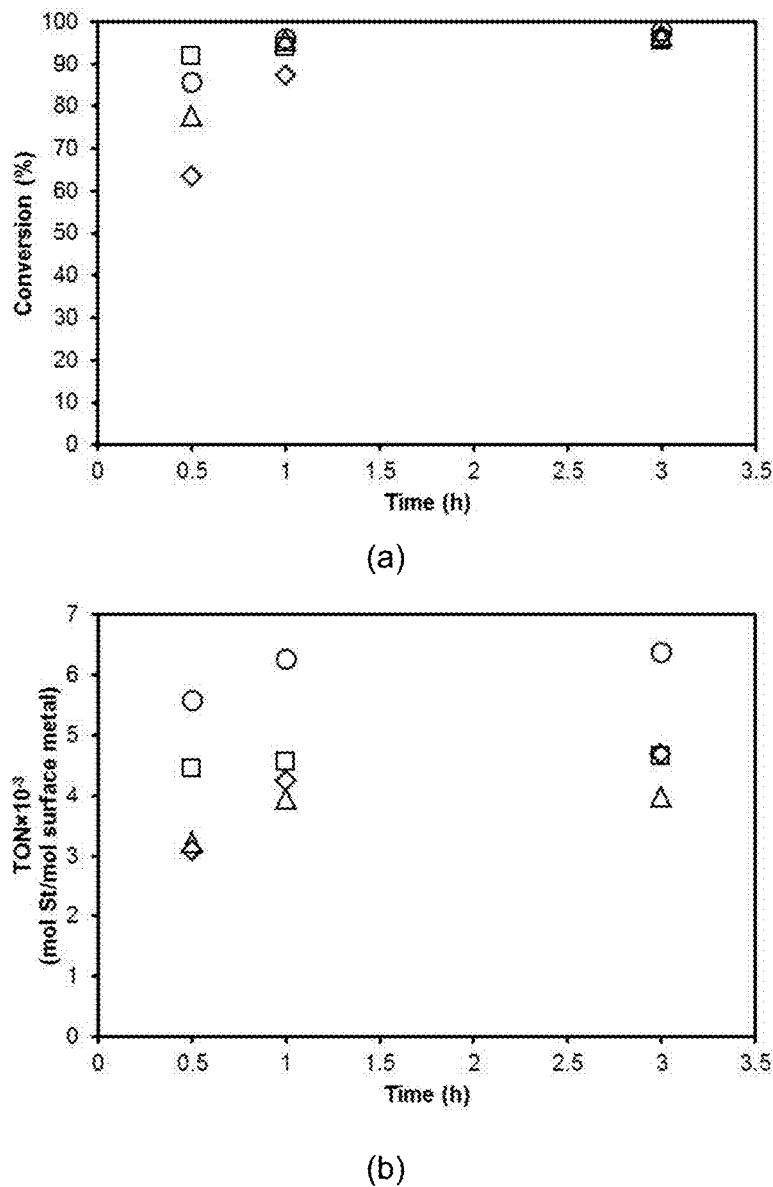
FIG. 3.5

METHODS OF MAKING SUPPORTED NI/PT BIMETALLIC NANOPARTICLES AND NI/PT MULTILAYER CORE-SHELL STRUCTURES AND THEIR USES FOR CO2 REFORMING

CROSS-REFERENCE TO RELATED APPLICATIONS

This application is the National Stage of International Application No. PCT/IB2014/003199, filed 17 Dec. 2014, having the title "METHODS OF MAKING SUPPORTED Ni/Pt BIMETALLIC NANOPARTICLES AND Ni/Pt MULTILAYER CORE-SHELL STRUCTURES AND THEIR USES FOR $CO_2$ REFORMING" which claims the benefit of and priority to U.S. Provisional Application entitled "SUPPORTED NiPt BIMETALLIC NANOPARTICLES, METHODS OF MAKING SUPPORTED NiPt BIMETALLIC NANOPARTICLES, AND APPLICATION OF THE SUPPORTED CATALYST FOR $CO_2$ REFORMING OF METHANE", having Ser. No. 61/917,395, filed on 18 Dec. 2013, the contents of all of which are incorporated by reference as if fully set forth herein.

BACKGROUND

In recent years the dry (carbon dioxide) reforming of methane (hereinafter "DRM") has received increasing interest in both academia and industry. From the environmental point of view, the DRM uses $CO_2$ and $CH_4$ as raw materials, which are the main components of greenhouse gas and are believed to be related to the global warming, to produce CO and $H_2$ (hereinafter "syngas"). Construction of DRM process units close to high $CO_2$ production place, e.g., power plant, and utilization of flue gas as feedstock are considered to be an effective way to reduce $CO_2$ emission. Additionally, syngas is an important intermediate for production of $H_2$ gas and downstream chemicals such as methanol, dimethyl ether and liquid hydrocarbons as an alternative for petroleum-derived hydrocarbons. Each target required a certain $H_2/CO$ molar ratio that will vary according to the process used to produce syngas. The DRM itself or in combination with other reforming techniques such as steam reforming of methane (hereinafter "SRM") and partial oxidation of methane (hereinafter "POM") can produce syngas with tunable $H_2/CO$ molar ratio to meet different demands. Applications of DRM in the other fields such as solar energy transmission system and production of high purity CO (Calcor process) are also widely investigated.

The SRM is a conventional and mature process in industry which is used to produce hydrogen on a worldwide basis. In this process, heterogeneous nickel-based materials are the most commonly used catalysts. This kind of catalysts is also known to be active for the DRM. However, some issues such as sintering, coke formation and metal oxidation, especially coke formation, leading to deactivation of the catalysts, seriously hinder the application of the DRM in industry. Actually, the same issues exist in the SRM, but it can be overcome efficiently by increasing the $H_2O/CH_4$ molar ratio in the feedstock. Compared to the SRM, due to increased C/H molar ratio in the feedstock, the DRM causes more significant coking.

Many efforts have been devoted to reduce or inhibit the coking in the DRM. Addition into the catalyst systems of alkali or alkaline earth metals as promoters, which are believed to promote the chemisorption and dissociation of $CO_2$ on the support, are widely investigated. The use of different support materials such as magnesia, ceria and zirconia, which are known to inhibit coking via different mechanisms, are also widely investigated. Bimetallic catalysts that uses synergistic effect of 2 different metals to create new chemical and physical properties, is another promising strategy to inhibit coking under DRM conditions. In that case, control of surface composition and overall catalyst structure are key parameters.

Bimetallic nanoparticles have attracted particular interests in the fields of catalysis and material science because of new properties such as improved activity, selectivity and stability, resulting from the interaction of two metals. For instance, in the case of naphta refroming process, supported ft-Pt catalysts are known to be more resistant to oxidative sintering than monometallic Ir catalysts, and supported Re—Pt catalysts are more tolerant to carbonaceous species than supported Pt.

Methods to prepare bimetallic nanoparticles can be divided into two types: physical (e.g., vacuum deposition, metal evaporation and sputtering) and chemical ones (e.g., co-impregnation and co-reduction). For both methods, there is a major challenge to precisely control particle size, size distribution, composition distribution and structure. Chemical methods, more attractive for very large-scale catalyst production, generally involve co- or successive impregnation methods for supported bimetallic nanoparticles and co- or successive reduction of two metal precursors in the presence of a stabilizer to prepare unsupported bimetallic nanoparticles in solution. However, due to the limit of preparation methods, a mixture involving monometallic nanoparticles of each metal and their alloys are typically obtained, and the structure of the final bimetallic nanoparticles, in particular surface composition and structure, is very difficult to control.

Thus, there is a need to produce catalyst systems in a controllable way so that the catalysts have a particular surface composition and structure.

SUMMARY

Embodiments of the present disclosure provide for supported Ni/Pt bimetallic nanoparticles, compositions including supported NiPt nanoparticles, methods of making supported NiPt nanoparticles, methods of using supported NiPt nanoparticles, and the like.

An embodiment of the present disclosure provides for a particle, among others, such as a supported Ni/Pt bimetallic nanoparticle having a Ni core and a Pt layer disposed on the surface of the Ni core, wherein the supported Ni/Pt bimetallic nanoparticle Pt/$Ni_s$ has a molar ratio of about 0.01 to 1, and wherein the supported Ni/Pt bimetallic nanoparticle is a refractory porous support. In an embodiment, a Ni layer can be disposed on the Pt layer and the Ni core. In an embodiment, a second Pt layer can be disposed over the Ni layer. The second Pt layer can also be disposed on Ni/Pt bimetallic nanoparticle.

An embodiment of the present disclosure provides for a method of making a supported Ni/Pt bimetallic nanoparticle, among others, that includes: heating a Ni/$Al_2O_3$ mixture to about 200 to 500° C. for about 1 to 5 hours to form nickel hydride on the surface of Ni nanoparticles to form a NiH/$Al_2O_3$ powder; and mixing the NiH/$Al_2O_3$ powder with a first solution including Pt for about 10 to 30 hours forming the supported Ni/Pt bimetallic nanoparticle. In one or more aspects, the first solution can be selected from: platinum (IV) chloride, ammonium hexachloroplatinate (IV), sodium hexachloroplatinate (IV) hexahydrate, potassium hexachloroplatinate (IV), or a combination thereof. In any one or more aspects, the method can further include mixing a second solution including Ni with the supported core-shell Ni/Pt bimetallic nanoparticle for about 10 to 30 hours to form a supported Ni/Pt/Ni multi-layer core shell nanoparticle. The second solution can be selected from: nickel nitrate hexahydrate, nickel chloride, or a combination thereof. In any one or more aspects, the method can further include mixing a third solution including Pt with the supported core-shell Ni/Pt/Ni bimetallic nanoparticle for about 10 to 30 hours to form a supported Ni/Pt/Ni/Pt multi-layer core shell nanoparticle.

An embodiment of the present disclosure provides for a particle, among others, that includes: exposing $CO_2$ to a supported Ni/Pt bimetallic nanoparticle; and $CO_2$ reforming of methane using the supported Ni/Pt bimetallic nanoparticle. In one or more aspects, the Ni/Pt bimetallic nanoparticle having a Ni core and a Pt layer can be disposed on the surface of the Ni core, wherein the supported Ni/Pt bimetallic nanoparticle $Pt/Ni_s$ has a molar ratio of about 0.01 to 1, and wherein the supported Ni/Pt bimetallic nanoparticle is a refractory porous support.

In any one or more aspects of the various embodiments, the average size of the particle can be about 3 to 15 nm. In any one or more aspects of the various embodiments, the refractory porous support can be selected from the group consisting of: $\gamma$-$Al_2O_3$, alumina, silica, zirconia, titania, and activated carbon. The supported Ni/Pt bimetallic nanoparticle can include a Ni layer disposed on the Pt layer and the Ni core, wherein the Ni layer has a coverage of about 1 to 100% of the supported Ni/Pt bimetallic nanoparticle.

Additional embodiments are described below. Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIG. 1.1 illustrates a graph of catalysts A to F that were characterized by CO-IR.

FIG. 1.2 illustrates typical STEM images of NiPt(0.71)/$Al_2O_3$ (a) before and (f) after thermal treatment. FIGS. 1.2(b), (c) and (e) illustrate HAADF-STEM images, the corresponding indexed fast Fourier transform (FFT) and EDX spectra of a selected single nanocrystal of untreated NiPt(0.71)/$Al_2O_3$. FIGS. 1.2(d) and (i) illustrates particle size distributions of NiPt(0.71)/$Al_2O_3$ before and after thermal treatment, respectively. FIGS. 1.2(g), (h) and (j) illustrate HAADF-STEM images, compositional line profile and EDX spectra of a selected NP of treated NiPt(0.71)/$Al_2O_3$.

FIG. 1.3 illustrates typical STEM images of NiPt(0.18)/$Al_2O_3$ (a) before and (f) after thermal treatment. FIGS. 1.3(b), (c) and (e) illustrates HAADF-STEM images, the corresponding indexed fast Fourier transform (FFT) and EDX spectra of a selected single nanocrystal of untreated NiPt(0.18)/$Al_2O_3$. FIGS. 1.3(d) and (i) illustrates particle size distributions of NiPt(0.18)/$Al_2O_3$ before and after thermal treatment, respectively. FIGS. 1.3(g), (h), and (j) HAADF-STEM image, compositional line profile and EDX spectra of a selected nanoparticle of treated NiPt(0.18)/$Al_2O_3$.

FIG. 1.4 illustrates typical STEM images of NiPt(0.66)/$Al_2O_3$ (a) before and (f) after thermal treatment. FIGS. 1.4(b), (c), and (e) illustrates HAADF-STEM images, the corresponding indexed fast Fourier transform (FFT) and EDX spectra of a selected single nanocrystal of untreated NiPt(0.66)/$Al_2O_3$. FIGS. 1.4(d) and (i) illustrate particle size distributions of NiPt(0.66)/$Al_2O_3$ before and after thermal treatment, respectively. FIGS. 1.4(g), (h), and (j) illustrates HAADF-STEM image, compositional line profile and EDX spectra of a selected nanoparticle of treated NiPt(0.66)/$Al_2O_3$.

FIG. 1.5 illustrates DRM reaction results that are summarized in Table 2 for catalyst D.

FIG. 2.1 illustrates infrared spectra of CO adsorbed on Ni/$Al_2O_3$ (a), Ni@Pt/$Al_2O_3$ (b), Ni@Pt@Ni/$Al_2O_3$ (c), and Pt/$Al_2O_3$ (d).

FIG. 2.2 illustrates STEM images and composition profiles of as-prepared Ni/$Al_2O_3$ (a and b), Ni@Pt/$Al_2O_3$ (c and d), and Ni@Pt@Ni/$Al_2O_3$ (e and f).

FIG. 2.3 illustrates magnetization curves of Ni/$Al_2O_3$ (□), Ni@Pt/$Al_2O_3$ (○), and Ni@Pt@Ni/$Al_2O_3$ (Δ).

FIG. 2.4 illustrates the syntheses of Ni/Pt bimetallic NPs are presented in Scheme 1.

FIG. 3.1 illustrates an STEM image of Ni/$Al_2O_3$ (a) and its particle size distribution (291 particles, average diameter=6.5±1.4 nm) (b).

FIG. 3.2 illustrates an STEM image of Ni@Pt/$Al_2O_3$ (a) and its particle size distribution (178 particles, average diameter=6.8±2.4 nm) (b).

FIG. 3.3 illustrates an STEM image of Ni@Pt@Ni/$Al_2O_3$ (a) and its particle size distribution (203 particles, average diameter=7.2±1.8 nm) (b).

FIG. 3.4 illustrates a TEM image of Pt/$Al_2O_3$ (a) and its particle size distribution (224 particles, average diameter=1.4±0.4 nm) (b).

FIG. 3.5 illustrates a conversion (a) and TON (b) as a function of reaction time in the hydrogenation of styrene catalysed by as-prepared metal NPs. (◇) Ni/$Al_2O_3$, (□) Ni@Pt/$Al_2O_3$, (Δ) Ni@Pt@Ni/$Al_2O_3$ and (○) Pt/$Al_2O_3$.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of material science, chemistry, physics, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure provide for supported Ni/Pt bimetallic nanoparticles, compositions including supported NiPt nanoparticles, methods of making supported NiPt nanoparticles, methods of using supported NiPt nanoparticles, and the like. In an embodiment, the supported Ni/Pt bimetallic nanoparticles can include multiple layers of metals and can be alternatively referred to as "Ni/Pt bimetallic multilayer core-shell nanoparticles". Embodiments of the supported Ni/Pt bimetallic nanoparticles can be used as catalysts and used in applications such as selective hydrogenation (e.g., of styrene), hydrogenolysis, dehydrogenation, isomerization, reforming (e.g., dry reforming of methane), cracking, CO oxidation, and fuel cell.

In an embodiment, the present disclosure includes supported Ni/Pt bimetallic nanoparticles having a Pt coverage ($Pt/Ni_s$ molar ratio) of about 0.01 to 1, about 0.1 to 0.9, about 0.5 to 0.95, or about 0.6 to 0.8 (e.g., about 1 to 100% coverage or about 10 to 90% coverage of the Ni surface). Embodiments of the present disclosure provide a supported Ni/Pt catalyst with the Pt coverage of about 0.7, which is a highly active catalyst for the DRM with a much higher selectivity and stability than typical Ni/Pt catalysts prepared by conventional methods.

In an embodiment, the support can be a refractory porous support. In an embodiment, the refractory porous support can be $\gamma$-$Al_2O_3$, alumina, zirconia, silica, titania, or an activated carbon. Example 1 describes an embodiment where the support is $\gamma$-$Al_2O_3$.

In an embodiment, the Ni/Pt bimetallic nanoparticle can be spherical or substantially spherical. In an embodiment, the Ni/Pt bimetallic nanoparticle can have a diameter of about 3 to 15 nm. In an embodiment, the Ni can have a diameter of about 2 to 15. In an embodiment, the Pt covered areas can have a thickness of Pt of about 0.3 to 1.5 nm.

Supported bimetallic catalysts are widely used in heterogeneous catalysis. But preparation of supported bimetallic catalysts with controllable composition and structure, especially controllable surface composition and structure, are difficult due to the limit of preparation methods (e.g., co-impregnation or successive impregnation methods). Embodiments of the present disclosure provide methods to prepare supported bimetallic catalysts with tunable composition and structure, especially surface composition and structure. In particular, methods to prepare supported bimetallic catalysts can include incipient wetness impregnation, dry impregnation, or deposition-precipitation.

Embodiments of the methods disclosed herein describe a new protocol to synthesize supported bimetallic catalysts and their composition and structure; especially surface composition and structure are readily controlled.

An embodiment discloses a method that is used to prepare supported Ni/Pt bimetallic multilayer core-shell nanoparticles, in which the core of the first metal is prepared by conventional incipient wetness impregnation method, for example, and the shell of the second metal is generated by surface organometallic chemistry on metals method. In an embodiment, the method of making a supported Ni/Pt bimetallic nanoparticle includes heating a $Ni/Al_2O_3$ mixture to about 200 to 500° C. or about 450° C. for about 1 to 5 hours or about 3 hours under hydrogen atmosphere to form a supported nickel nanoparticles presenting surface nickel hydride species ($NiH/Al_2O_3$). Subsequently, the $NiH/Al_2O_3$ powder is mixed with a first solution including Pt for about 10 to 30 hours or about 20 hours forming the supported Ni/Pt bimetallic nanoparticles. Once formed, the supported Ni/Pt bimetallic nanoparticles can be rinsed, washed, and dried as needed. Additional details are provided in the Examples.

In an embodiment, the first solution can be selected from: platinum (IV) chloride, ammonium hexachloroplatinate (IV), sodium hexachloroplatinate (IV) hexahydrate, potassium hexachloroplatinate (IV), or a combination thereof.

Coke formation, leading to deactivation of catalysts, is one of the main issues that hinder the practical development of the DRM process at an industrial scale. Embodiments of the present disclosure are highly resistant against the coke formation in the process of the DRM. In an embodiment, a catalyst system for improved coke resistance in the DRM can include a Ni/Pt bimetallic nanoparticle. The catalyst system disclosed herein is considered as an alternative to the conventional nickel-based reforming catalysts, for the processes of DRM, SRM, POM or their combinations. The controlled coverage of Ni nanoparticles allows the reduction of the use of noble metal (Pt) to its minimum and therefore limits the cost of the catalyst. An embodiment of the catalyst system is highly active under DRM conditions.

As mentioned above, the supported Ni/Pt bimetallic nanoparticle also includes a supported Ni/Pt bimetallic multilayer core-shell nanoparticle, where one or more layers of Ni or Pt are added to the Ni/Pt nanoparticle. As noted above, the first Pt layer can have less than 100% coverage, but can also have 100% coverage of the supported Ni/Pt bimetallic multilayer core-shell nanoparticle. Each successive layer can have from about 1 to 100%, about 10 to 90%, about 30 to 90%, about 40 to 80%, or about 60 to 80% surface coverage.

The core diameter and shell thickness are tunable depending on the desired characteristics of the supported Ni/Pt bimetallic multilayer core-shell nanoparticles. In an embodiment, the Ni/Pt bimetallic multilayer core-shell nanoparticle can have a diameter of about 3 to 15. In an embodiment, the Ni core can have a diameter of about 3 to 15 nm. In an embodiment, each shell layer (Ni or Pt) can have a thickness of about 0.3 to 1.5 nm.

Another embodiment of the present disclosure describes a facile method to prepare bimetallic multilayer core-shell nanoparticles with tunable structures, in which a monometallic catalyst with well-defined structure is first synthesized using a conventional incipient wetness impregnation method, and then the second metal is selectively deposited on the parent metal surface through controllable reduction of a second metal precursor using surface organometallic chemistry on metals method. This last step can be repeated in order to add additional shells of a different metal on the surface of the bi-metallic core-shell nanoparticle. Additional details are provided in the Example 2.

In addition to the method described above in reference to forming the supported Ni/Pt bimetallic nanoparticle, the method for forming the supported Ni/Pt bimetallic multilayer core-shell nanoparticle includes the additional step(s) of mixing a second solution including Ni with the supported Ni/Pt bimetallic nanoparticle for about 10 to 30 hours or about 20 hours to form a supported Ni/Pt bimetallic core shell nanoparticle. In an embodiment, the second solution can be selected from: nickel nitrate hexahydrate, nickel chloride, or a combination thereof. Additional layers can be added in a similar manner as the Ni layer is added. In an embodiment, the layers are alternated between Ni and Pt. Once formed, the supported Ni/Pt bimetallic core shell nanoparticles can be rinsed, washed, and dried as needed. Additional details are provided in the Examples.

The supported Ni/Pt bimetallic multilayer core-shell nanoparticle systems disclosed herein have been tested as catalysts for hydrogenation of styrene and exhibit high catalytic activities and selectivities. These catalyst systems can also be considered as active catalysts for other potential applications such as selective hydrogenation, hydrogenolysis, dehydrogenation, isomerization, reforming, cracking, CO oxidation, and fuel cell. In an embodiment, the supported Ni/Pt bimetallic multilayer core-shell nanoparticles are active catalysts for hydrogenation of styrene with high selectivity.

EXAMPLES

Example 1

Example 1 discloses a series of supported Ni/Pt bimetallic catalyst with a Pt coverage (Pt/Ni$_s$ molar ratio) in the range of 0.1 to 0.9 (catalysts A to F, see Table 1). Example 1 also discloses a method that is used to prepare supported bimetallic catalysts with controlled composition and structure, especially surface composition and structure. Example 1 also discloses a process for the DRM using the catalyst disclosed herein. Materials and general consideration:

All manipulations dealing with air- or moisture-sensitive materials were carried out under argon atmosphere. Unless otherwise stated, all reagents were purchased from commercial suppliers and used as received. Toluene was purified by the MBRAUN solvent purification system. γ-Al$_2$O$_3$ (Aeroxide® Alu C, fumed aluminum oxides, specific surface area 130±15 m2/g) was purchased from Evonik Industries. Prior to use, γ-Al$_2$O$_3$ was aggregated by treatment with distilled water and dried in the oven at 120° C. for 2 days. The void volume of γ-Al$_2$O$_3$ is 0.5 ml/g, determined by water impregnation. Pt(acac)$_2$ (97%) was purchased from Sigma-Aldrich and used as received. The CO (99.998%) and hydrogen (99.999%) gases were purchased from Abdullah Hashim Industrial Gases & Equipment Co. Ltd. (Jeddah) and used as received. Ni/Al$_2$O$_3$ was prepared according to the procedure reported in the literature (See, Appl. Catal. A: Gen. 323 (2007) 188-201; Appl. Catal. A: Gen. 366 (2009) 122-129, each of which is incorporated herein by reference). Its Ni loading is 10 wt %, determined by elemental analysis.

Elemental analyses were obtained from the service of Mikroanalytisches Labor Pascher (Remagen, Germany). The CO-IR spectra were recorded on a Nicolet 6700 FT-IR spectrometer with a resolution of 4 cm$^{-1}$. The samples were first diluted 2-3 times with γ-Al$_2$O$_3$ (thermally treated at 500° C. under vacuum over 12 h) and then pressed to pellets (ca. 0.1-0.2 g). The sample pellets were mounted in a sample holder, which was placed in an IR cell. The CO gas (20-30 mmHg) was fed into the IR cell, kept for 5 min and then evacuated under vacuum for 10 min. The CO-IR spectra were presented by subtraction of the spectra recorded before and after the CO absorption. High-angle annular dark-field scanning transmission electron microscopy (HAADF-STEM) and energy-dispersive X-ray spectroscopy (EDX) were performed on a Titan G2 60-300 CT electron microscope by operating it at the accelerating voltage of 300 kV. The samples were prepared by depositing a drop of dilute sample solution on a carbon-coated copper grid and dried at room temperature.

To prepare Ni/Al$_2$O$_3$, a typical procedure is described as follows: for instance, in the case of catalyst A, 1.0 g of Ni/Al$_2$O$_3$ was treated at 450° C. for 3.0 h in a hydrogen flow (300 ml/min) and cooled down to room temperature under hydrogen atmosphere. The powder was transferred into a 100-mL Schlenk flask under hydrogen protection. 50 ml of toluene solution of Pt(acac)$_2$ (18.9 mg, 0.048 mmol) was added and the mixture was stirred at room temperature for 20 h under hydrogen (1 atm). After filtering, washing with toluene (3×30 ml) inside the glovebox, and drying under vacuum, brown powder was isolated and kept inside the glovebox. Yield: 86%.

A step of this synthesis is the controlled reduction of Pt(acac)$_2$ over Ni NP surface. Due to the difference of reduction potentials of Pt$^{2+}$ ($E^0(Pt^{2+}/Pt^0)$=+1.188 V), H$^+$ ($E^0(H^+/H_2)$=0 V) and Ni$^{2+}$ ($E^0(Ni^{2+}/Ni^0)$=−0.25 V),[8] two possible side reactions are possible: the direct reduction of Pt(acac)$_2$ by molecular hydrogen in solution and oxidation of Ni by Pt(acac)$_2$ over Ni NP surface. The former would cause formation of monometallic Pt NPs, and the latter would give rise to dissolution of Ni$^0$ into Ni$^{2+}$, and both are detrimental to control composition and structure of bimetallic NPs. Blank tests (Pt(acac)$_2$, 30 mg; toluene, 20 ml; H$_2$, 1.0 atm; 22 or 50° C., 20 h) has proved that direct reduction of Pt(acac)$_2$ by molecular hydrogen in solution is considerably pronounced at 50° C., but it was dramatically suppressed at room temperature (ca. 22° C.). Therefore, room temperature is an optimized temperature for the preparation of Ni-c/Pt-s/Al$_2$O$_3$. In order to prevent oxidation of Ni by Pt(acac)$_2$, we first thermally treated Ni/Al$_2$O$_3$ under hydrogen to form the Ni$_x$H/Al$_2$O$_3$, in which the formed Ni hydride layer may effectively prevent direct contact of Pt(acac)$_2$ with Ni NP surface. The formed Ni$_x$H/Al$_2$O$_3$ also exhibits high reactivity toward the reduction of Pt(acac)$_2$. Therefore Pt(acac)$_2$ is selectively reduced on the surface Ni nanoparticles surface.

TABLE 1

Properties of catalysts A to F

| Catalyst | Ni (wt %) | Pt (wt %) | $Ni_xPt_{100-x}$ (molar ratio) | $Pt/Ni_s$[a] (molar ratio) |
|---|---|---|---|---|
| A | 9.14 | 0.75 | $Ni_{98}Pt_{02}$ | 0.18 |
| B | 9.39 | 1.29 | $Ni_{96}Pt_{04}$ | 0.29 |
| C | 8.96 | 2.63 | $Ni_{92}Pt_{08}$ | 0.63 |
| D | 8.83 | 2.93 | $Ni_{91}Pt_{09}$ | 0.71 |
| E | 9.05 | 3.32 | $Ni_{90}Pt_{10}$ | 0.78 |
| F | 8.81 | 3.54 | $Ni_{89}Pt_{11}$ | 0.86 |

[a]Pt and Ni contents were obtained from elemental analysis, and $Ni_s$ refers to the surface nickel atoms. The amount of surface nickel atoms was calculated from the formula: $Ni_s$ = $Ni_{total}$ × D, where $Ni_{total}$ is the amount of the total nickel atoms and D is the dispersion. D was calculated from the following formula: % D = 97.1/d (assuming in a first approximation that Ni NPs are spherical, C. H. Bartholomew and R. B. Pannell, J. Catal. 65 (1980), 390-401), where d is the average particle diameter determined by TEM.

Catalysts A to F were characterized by CO-IR and the results are given in FIG. 1.1. It is apparent that the CO absorption bands on pure Ni and Pt NPs are strikingly different. For the Ni NPs, three absorption bands 2065, 2037 and 1942 $cm^{-1}$ (see FIG. 1.1, $Ni/Al_2O_3$) were observed, which are assigned to subcarbonyl ($Ni(CO)_x$, x=2 or 3), linear (NiCO) and bridged ($Ni_2CO$) species, respectively. For the Pt NPs, two absorption bands 2065 and 1810 $cm^{-1}$ (see FIG. 1.1, $Pt/Al_2O_3$) were observed, which are ascribed to linear (PtCO) and bridged ($Pt_x(CO)$, x=2.3) species, respectively, and the former is very strong and the latter very weak. As the Ni NPs were covered with increasing amount of Pt (FIG. 1.1, sample A to F), the absorption bands characteristic on Ni NPs disappeared and the bands characteristic of Pt increase accordingly.

FIG. 1.2 displays the typical STEM and HRTEM images of NiPt(0.71)/$Al_2O_3$ before and after thermal treatment. The similar images were also observed for NiPt(0.18)/$Al_2O_3$ and NiPt(0.66)/$Al_2O_3$ (see FIGS. 1.3 and 1.4). For the untreated samples, EDX analyses of tens of individual particles for each sample revealed no monometallic Ni or Pt particles, which prove the advantage of our preparation protocol to synthesize "pure" bimetallic NPs. A typical EDX spectrum for the selected single nanocrystal of NiPt(0.71)/$Al_2O_3$ is shown in FIG. 1.2e. The detectable interplanar distances (d{111}=1.94-2.05 Å and d{002}=1.70-1.80 Å) characteristic on a regular face-centered cubic (fcc) nickel crystal imply that the Ni NPs remain unchanged during the preparation. It can also be observed in FIGS. 2b and 2c that, the exposed surfaces mainly consist of the {111} and {100} facets, being consistent with those expected from the truncated cuboctahedron model for the fcc metal NPs (e.g., Ni and Pt).[41] Since the brightness is proportional to the square of atomic number Z of an element on the STEM images, the Pt atoms are much brighter than Ni atoms owing to its larger atomic number. It can be clearly observed in FIG. 1.2b that the brighter Pt atoms are well dispersed on the Ni surface in an atomic pattern. For the treated samples, it is apparent that the thermal treatment has no significant effects on the particle sizes, as observed in FIGS. 1.2d and 1.2i (and also in FIGS. 1.3 and 1.4). The same EDX analyses ruled out the presence of the monometallic Ni or Pt NPs. FIG. 1.2j shows a typical EDX spectrum for the selected NP of NiPt(0.71)/$Al_2O_3$. It can be seen from FIGS. 1.2f and 1.2g that all the bimetallic NPs are partially covered with "thin and brighter" outmost layers. The compositional line profile analysis depicted in FIG. 1.2h demonstrates that these outmost layers are Pt-enriched.

A typical DRM test is described as follows: 50 mg of catalyst and 150 mg of SiC as diluent (SiC/catalyst=3) are mixed and introduced into a quartz reactor. The reactor is then mounted in the DRM set-up. Catalyst mixture is heated up to 500° C. (heating rate, 10° C./min) under $H_2$/Ar flow ($H_2$, 10 vol %; 40 ml/min) and kept at 500° C. for 3 h. Then the reactor is purged by argon flow (100 ml/min) and heated up to the desired reaction temperature (700° C.). The reactant gases ($CH_4/CO_2/N_2$=1/1/8, P=1 atm) are introduced to the reactor at a total flow of 100 ml/min (WHSV=120 L·$h^{-1}$·g $cat^{-1}$). Reactants and products are continuously monitored using an on-line gas chromatography. After the test, catalysts are collected and characterized by TEM and elemental analysis. The DRM reaction results are summarized in Table 2 and the complete test is plotted on FIG. 1.5 for catalyst D. Covering Ni nanoparticle with Pt increases the stability by reducing coke formation, with the lowest coke formation for catalyst D corresponding to 70% of Ni surface coverage by Pt atoms. Catalyst D show almost no deactivation and elemental analysis reveal below 1% of coke formation after 50 hours of under DRM conditions.

TABLE 2

Results for the DRM tests[a]

| | Initial | | | After 20 h | | | |
|---|---|---|---|---|---|---|---|
| Catalyst | $CH_4$ (%) | $CO_2$ (%) | $H_2$/CO | $CH_4$ (%) | $CO_2$ (%) | $H_2$/CO | Coke (wt %) |
| A | 59 | 88 | 0.85 | 43 | 71 | 0.75 | 6.92[b] |
| B | 75 | 81 | 0.93 | 57 | 64 | 0.83 | 4.82 |
| C | 73 | 77 | 0.91 | 60 | 67 | 0.85 | 3.50 |
| D | 89 | 90 | 0.99 | 86 | 89 | 0.98 | 0.82[c] |
| E | 81 | 91 | 0.91 | 70[d] | 80[d] | 0.89[d] | 3.77[d] |
| F | 63 | 88 | 0.87 | 46 | 73 | 0.80 | 19.7[e] |
| EQ[e] | | | | 88 | 92 | 0.95 | |

[a]General catalytic conditions: P = 1 atm, T = 700° C., $CH_4/CO_2/N_2$ = 1:1:8, GHSV = 120 L $h^{-1}$ g $cat^{-1}$.
[b]24 h;
[c]49 h;
[d]18.0 h.
[e]42 h.
[e]Thermodynamic equilibrium composition: Conversion($CH_4$) = 88.0%, Conversion($CO_2$) = 92.4%, $H_2$/CO = 0.95, calculated using the commercial software THERBAL under considering a system comprising DRM and reverse water-gas shift reaction (RWGS) (700° C., $CH_4/CO_2/N_2$ = 1:1:8).

Example 2

Extended from the synthesis described above, below it is presented a facile method to prepare alumina-supported Ni/Pt core-shell bimetallic NPs (Ni-c/Pt-s/$Al_2O_3$) and multi-layer core-shell NPs (Ni-c/Pt-s/Ni-s/$Al_2O_3$) using modified surface organometallic chemistry on metals method. Since the reduction potential of $Ni^{2+}$ is lower than those of $Pt^{2+}$ and $H^+$, direct reduction of Ni(acac)$_2$ by molecular hydrogen in solution and oxidation of Pt by Ni(acac)$_2$ over the particle surface are not assumed to take place. Therefore, Ni(acac)$_2$ react with surface platinum hydride formed in-situ by the reaction of Ni-c/Pt-s/$Al_2O_3$ with hydrogen, to selectively form a Ni layer over the nanoparticles. Finally, the Ni-c/Pt-s/Ni-s/$Al_2O_3$ with multi-layer core-shell structure is obtained. The shell thickness of Ni can be modified by addition of excess Ni(acac)$_2$, e.g., Ni(acac)$_2$/Pt=2.0. The obtained bimetallic multi-layer core-shell NPs are characterised by elemental analysis, Infrared spectroscopy of absorbed carbon monoxide (CO-IR), high-angle annular dark-field scanning transmission electron microscopy (HAADF-STEM) and energy-dispersive X-ray spectroscopy (EDX) techniques. As an example, these bimetallic NPs are shown to be active for selective hydrogenation of styrene.

This is the first example of alumina-supported Ni/Pt multi-layer core-shell NPs although alumina-supported Ni or Pt monometallic or their alloy NPs have been widely used in heterogeneous catalysis.[5] Similar approaches known as "hydrogen sacrificial" and "catalytic reduction" method have been employed to prepare respectively bimetallic colloids by Toshima's group,[9] and supported bimetallic NPs in aqueous phase in the Marecot's group,[10] In both groups, special attention has been paid to avoid oxidation of the parent metal by the second metal but attempts to increase the Pt shell thickness of Ni-c/Pt-s/Al$_2$O$_3$ by addition of excess Pt(acac)$_2$ (e.g., Pt/Ni$_s$=2 or 5) failed and Pt/Ni$_s$ never exceed the unity. It implies that reduction of Pt(acac)$_2$ cannot take place on the newly-formed Pt shell, which was further confirmed by the failure of reduction of Pt(acac)$_2$ on as-prepared Pt/Al$_2$O$_3$ under the same conditions. However, Ni(acac)$_2$ was successfully reduced on the surface of Ni-c/Pt-s/Al$_2$O$_3$ (see below). According to their reduction potentials, Pt(acac)$_2$ should be more readily reduced than Ni(acac)$_2$, but the result is opposite. The reason why Pt(acac)$_2$ and Ni(acac)$_2$ show such different reactivity on the surface of Pt still remains unclear.

Syntheses of Ni/Pt bimetallic NPs are presented in Scheme 1, FIG. 2.4. Initially, alumina-supported Ni NPs (Ni/Al$_2$O$_3$) were prepared according to the classical methods[6] and characterised by STEM, showing evenly dispersed Ni NPs over alumina with an average diameter of 6.5±1.4 nm (see FIG. 3.1, Supporting Information as described in Example 1). Treatment of Ni/Al$_2$O$_3$ at 450° C. for 3 h under hydrogen flow and then cooling down to room temperature under hydrogen give Ni NPs covered with hydrogen (Ni$_s$H/Al$_2$O$_3$). Reaction of Ni$_s$H/Al$_2$O$_3$ with Pt(acac)$_2$ (acac=acetylacetonate) (Pt/Ni$_s$=1.0),[7] in toluene at room temperature under hydrogen (1 atm) for 20 h, leads to core-shell NPs Ni-c/Pt-s/Al$_2$O$_3$ with an average diameter of 6.8±2.4 nm (see FIG. 3.2) (Pt/Ni$_s$=0.94, calculated from elemental analysis result assuming that, at such moderate temperature, the Ni core remains intact during the preparation). Further reaction of Ni-c/Pt-s/Al$_2$O$_3$ with Ni(acac)$_2$, (Ni(acac)$_2$/Pt≈2.0) under the same reaction conditions gives rise to super core-shell NPs Ni-c/Pt-s/Ni-s/Al$_2$O$_3$ in almost a stoichiometric yield. Its average diameter is 7.2±1.8 nm (see FIG. 3.3).

The core-shell structures of bimetallic NPs Ni-c/Pt-s/Al$_2$O$_3$ and Ni-c/Pt-s/Ni-s/Al$_2$O$_3$ were confirmed by CO-IR and STEM techniques. The CO-IR spectra of Ni/Pt bimetallic NPs, along with pure Ni and Pt NPs, are shown in FIG. 2.1. It is apparent that the CO absorption bands on pure Ni and Pt NPs are strikingly different. For the Ni NPs, three absorption bands at 2065, 2037 and 1942 cm$^{-1}$ (see FIG. 2.1a) are assigned to subcarbonyl (Ni(CO)$_x$, x=2 or 3), linear (NiCO) and bridged (Ni$_2$CO) species, respectively.[11] For the Pt NPs, two absorption bands at 2065 and 1810 cm$^{-1}$ (see FIG. 2.1d) were observed, which are ascribed to linear (PtCO) and bridged (Pt$_x$(CO), x=2,3) species, respectively, and the former has a very high intensity whereas the latter has a very weak one.[12] As the Ni NPs were covered by Pt layer to form core-shell structure in the sample Ni-c/Pt-s/Al$_2$O$_3$, the absorption bands characteristic on Ni NPs disappeared and the bands on Pt NPs were exclusively observed (see FIG. 2.1b). Since the coverage of Pt over the Ni NPs is close to unity (Pt/Ni$_s$=0.94), it can be inferred that in the sample Ni-c/Pt-s/Al$_2$O$_3$ the shell is comprised of a Pt monolayer without strong modification of the Pt properties by subjacent Ni core. Further coating of this core-shell NPs by Ni layer to form multi-layer core-shell structure in the sample Ni-c/Pt-s/Ni-s/Al$_2$O$_3$ results in the exclusive absorption bands characteristic on Ni NPs (see FIG. 2.1c).

The bimetallic NPs were also analysed by STEM coupled with EDX. EDX analyses of tens of individual particles of both bimetallic NPs does not reveale monometallic Ni or Pt particles. The typical STEM images of bimetallic NPs, along with the monometallic Ni NPs as reference, are presented in FIG. 2.2 and FIGS. 3.1-3.3. A clear contrast difference on the STEM images, in which the brightness is proportional to the square of atomic number Z of an element, demonstrates the presence of the core-shell structures in the bimetallic NPs (see FIGS. 2.2c and e). The Pt shell is brighter owing to its larger atomic number, whereas the Ni core and shell is relatively darker. This result is consistent with their composition profiles. As displayed in FIGS. 2.2d and f, Ni-c/Pt-s/Al$_2$O$_3$ shows two peaks in the outer layer due to the presence of the Pt shell, whereas in the Ni-c/Pt-s/Ni-s/Al$_2$O$_3$ two shoulder peaks on either side of these two peaks are present owing to the coating of Ni-c/Pt-s/Al$_2$O$_3$ by another Ni layer.

FIG. 2.3 displays magnetic hysteresis curves of Ni/Al$_2$O$_3$, Ni-c/Pt-s/Al$_2$O$_3$ and Ni-c/Pt-s/Ni-s/Al$_2$O$_3$, which were measured at room temperature. The magnetisation is presented with respect to the Ni content. The S-shaped field-dependent magnetisation and the absence of coercive field indicate dominant superparamagnetic behaviours of these three samples. Due to the addition of Pt, the saturation magnetisation of bimetallic NPs is slightly lower than that of monometallic Ni NPs. The core-shell structure seems to have no effect on magnetic properties of NPs.

Preliminary tests show that these Ni/Pt NPs are active catalysts for hydrogenation of styrene with high selectivity for ethylbenzene, (>99%). The results are given in FIG. 3.5 and Table S1. As shown in FIG. 3.5(a), the conversion increases in the following order Ni/Al$_2$O$_3$<Ni-c/Pt-s/Ni-s/Al$_2$O$_3$<Pt/Al$_2$O$_3$<Ni-c/Pt-s/Al$_2$O$_3$. It seems that the NPs with the Pt outer layers are more active than those with the Ni outer layers and the bimetallic NPs lead to higher catalytic activities. A comparable tendency was observed upon considering the dispersion of NPs (see FIG. 3.5(b)). The NPs with the Pt outer layers show higher catalytic activities than those with the Ni outer layers, and Pt/Al$_2$O$_3$ is more active than Ni-c/Pt-s/Al$_2$O$_3$ presumably due to its higher dispersion (see FIGS. 3.2 and 3.4). By comparison with other alumina-supported Ni/Pt bimetallic NPs prepared by successive impregnation method,[13] it can be found that our bimetallic NPs are more active.

In summary, we report here a protocol to prepare alumina-supported bimetallic NPs using SOMC on metals method. Ni/Pt bimetallic multilayer core-shell NPs (Ni-c/Pt-s/Al$_2$O$_3$) and multi-layer core-shell (Ni-c/Pt-s/Ni-s/Al$_2$O$_3$) were prepared and characterised by CO-IR and STEM techniques. The experimental results have demonstrated that SOMC on metals method is a powerful tool to selectively decorate the surface structure of metal NPs. The obtained bimetallic NPs exhibit high catalytic activities for hydrogenation of styrene.

Example 2 References

1 A. M. Henning, J. Watt, P. J. Miedziak, S. Cheong, M. Santonastaso, M. Song, Y. Takeda, A. I. Kirkland, S. H. Taylor and R. D. Tilley, *Angew. Chem. Int. Ed.,* 2013, 52, 1477-1480; L. Gan, M. Heggen, S. Rudi and P. Strasser, *Nano Lett.,* 2012, 12, 5423-5430; L. Wang and Y. Yamauchi, *J. Am. Chem. Soc.,* 2010, 132, 13636-13638.
2 C.-H. Jun, Y. J. Park, Y.-R. Yeon, J. Choi, W. Lee, S. Ko and J. Cheon, *Chem. Commun.,* 2006, 1619-1621.

3 R. Mu, Q. Fu, H. Xu, H. Zhang, Y. Huang, Z. Jiang, S. Zhang, D. Tan and X. Bao, *J. Am. Chem. Soc.*, 2011, 133, 1978-1986.

4 K. Pelzer, J.-P. Candy, G. Godard and J.-M. Basset, in *Nanoparticles and Catalysis*, ed. D. Astruc, Wley-VCH, Weinheim, 2008, pp. 553-620.

5 W. Yu, M. D. Porosoff and J. G. *Chen, Chem. Rev.*, 2012, 112, 5780-5817; C. Liu, J. Ye, J. Jiang and Y. Pan, *Chem Cat Chem*, 2011, 3, 529-541.

6 F. Negrier, E. Marceau, M. Che and D. de Caro, *C. R. Chimie*, 2003, 6, 231-240; F. Negrier, E. Marceau and M. Che, *Chem. Commun.*, 2002, 1194-1195.

7 The amount of surface nickel atoms of Ni/Al$_2$O$_3$ was calculated from the formula: $Ni_s = Ni_{total} \times D$, where $Ni_s$ is the amount of surface nickel atoms, $Ni_{total}$ is the amount of the total nickel atoms and D is the dispersion of Ni NPs. D was calculated from the following formula: %D=97.1/d (assuming in a first approximation that Ni NPs are spherical, C. H. Bartholomew and R. B. Pannell, *J. Catal.*, 1980, 65, 390-401), where d is the average particle diameter determined by TEM. The calculated D value (14.9%) is comparable with that obtained from hydrogen chemisorption (12.6%).

8 Wikipedia, http://en.wikipedia.org/wiki/Table_of_standard_electrode_potentials.

9 Y. Wang and N. Toshima, *J. Phys. Chem. B*, 1997, 101, 5301-5306.

10 C. L. Pieck, P. Marecot and J. Barbier, *Appl. Catal. A-Gen.*, 1996, 145, 323-334; C. L. Pieck, P. Marecot and J. Barbier, *Appl. Catal. A-Gen.*, 1996, 141, 229-244.

11 C. H. Bartholomew and R. B. Pannell, *J. Catal.*, 1980, 65, 390-401; M. Primet, J. A. Dalmon and G. A. Martin, *J. Catal.*, 1977, 46, 25-36.

12 S. D. Jackson, B. M. Glanville, J. Willis, G. D. McLellan, G. Webb, R. B. Moyes, S. Simpson, P. B. Wells and R. Whyman, *J. Catal.*, 1993, 139, 207-220; R. Barth, R. Pitchal, R. L. Anderson and X. E. Verykios, *J. Catal.*, 1989, 116, 61-70.

13 C. Betti, J. Badano, M. J. Maccarrone, V. Mazzieri, C. Vera and M. Quiroga, *Appl. Catal. A-Gen.*, 2012, 435-436, 181-186.

Supporting Information for Example 2:

Experimental Section

General consideration: All manipulations dealing with air- or moisture-sensitive materials were carried out under argon atmosphere. Unless otherwise stated, all reagents were purchased from commercial suppliers and used as received. Toluene was purified by the MBRAUN solvent purification system. Styrene (Sigma-Aldrich, purity >99%) was purified over calcium hydride and distilled off under vacuum prior to use. γ-Al$_2$O$_3$ (Aeroxide® Alu C, fumed aluminium oxides, specific surface area 130±15 m$^2$/g) was purchased from Evonik Industries. Prior to use, γ-Al$_2$O$_3$ was aggregated by treatment with distilled water and dried in the oven at 120° C. for 2 days. The void volume of γ-Al$_2$O$_3$ is 0.5 ml/g, determined by water impregnation. Pt(acac)$_2$ (97%), Ni(acac)$_2$ (95%), Pt(NH$_3$)$_4$(OH)$_2$ (98%) and n-decane (99%) were purchased from Sigma-Aldrich and used as received. The CO (99.998%) and hydrogen (99.999%) gases were purchased from Abdullah Hashim Industrial Gases & Equipment Co. Ltd. (Jeddah) and used as received. Ni/Al$_2$O$_3$ was prepared according to the procedure reported in the literature (*Chimie*, 2003, 6, 231-240; *Chem. Commun.*, 2002, 1194-1195). Its Ni loading is 5.66 wt %, determined by elemental analysis.

Elemental analyses were obtained from the service of Mikroanalytisches Labor Pascher (Remagen, Germany). Ni metal dispersion was measured on fresh samples from uptakes of weakly and strongly chemisorbed H$_2$ at 303 K (150-300 mmHg) using a ASAP 2020C chemisorption analyzer, after reducing samples at 723 K for 2 h and evacuating at 723 K for 2 h within the adsorption cell. Ni dispersion was calculated using 1:1 H:Ni titration stoichiometry. The CO-IR spectra were recorded on a Nicolet 6700 FT-IR spectrometer with a resolution of 4 cm$^{-1}$. The samples were first diluted 2-3 times with γ-Al$_2$O$_3$ (thermally treated at 500° C. under vacuum over 12 h) and then pressed to pellets (ca. 0.1-0.2 g). The sample pellets were mounted in a sample holder, which was placed in an IR cell. The CO gas (20-30 mmHg) was fed into the IR cell, kept for 5 min and then evacuated under vacuum for 10 min. The CO-IR spectra were presented by subtraction of the spectra recorded before and after the CO absorption. High-angle annular dark-field scanning transmission electron microscopy (HAADF-STEM) and energy-dispersive X-ray spectroscopy (EDX) were performed on a Titan G$^2$ 60-300 CT electron microscope by operating it at the accelerating voltage of 300 kV. The samples were prepared by depositing a drop of dilute sample solution on a carbon-coated copper grid and dried at room temperature. The magnetic hysteresis loops of the samples were recorded using a commercial Quantum Design Magnetic Property Measurement System with Superconducting Quantum Interference Device technology (MPMS® SQUID VSM) at room temperature from −5 Tesla to 5 Tesla.

Synthesis of Pt/Al$_2$O$_3$: Pt/Al$_2$O$_3$ was synthesized using incipient wetness impregnation method. A 5 ml solution of Pt(NH$_3$)$_4$(OH)$_2$ (0.51 g) in deionized water was added to 10 g of γ-Al$_2$O$_3$. The mixture was placed at room temperature overnight and then dried in the oven at 100° C. for 2.0 h. The obtained solid was treated under a flow of air (100 ml/min) up to 500° C. (heating rate=7.5° C./min) and kept for 5.0 h at 500° C., followed by treatment under a flow of hydrogen (300 ml/min) at 400° C. for 5.0 h. Finally, brown powder was isolated and kept inside the glovebox. Elemental analysis: Pt, 3.02 wt %.

Synthesis of Ni-c/Pt-s/Al$_2$O$_3$: 1.0 g of Ni/Al$_2$O$_3$ was treated at 450° C. for 3.0 h in a hydrogen flow (300 ml/min) and cooled down to room temperature at hydrogen atmosphere. The powder was transferred into a 100-mL Schlenk flask under hydrogen protection. 50 ml of toluene solution of Pt(acac)$_2$ (55 mg, 0.14 mmol) was added and the mixture was stirred at room temperature for 20 h under hydrogen (1 atm). After filtering, washing with toluene (3×30 ml) inside the glovebox, and drying under vacuum, brown powder was isolated and kept inside the glovebox. Yield: 92%. Elemental analysis: Ni, 5.21 wt %; Pt, 2.37 wt %.

Synthesis of Ni-c/Pt-s/Ni-s/Al$_2$O$_3$: A 100-mL Schlenk flask containing 1.0 g of Ni-c/Pt-s/Al$_2$O$_3$ was evacuated and refilled with hydrogen. 30 ml of toluene solution of Ni(acac)$_2$ (72 mg, 0.28 mmol) was added and the mixture was stirred at room temperature for 20 h under hydrogen (1 atm). After filtering, washing with toluene (3×30 ml) inside the glovebox, and drying under vacuum, brown powder was isolated and kept inside the glovebox. Yield: 96%. Elemental analysis: Ni, 6.68 wt %; Pt, 2.31 wt %.

Catalytic test: The given amounts of catalyst (50 mg), toluene (75 ml), styrene (4 ml, 35 mmol) and n-decane as internal standard (1.4 ml, 7 mmol) were added to a 150-mL stainless steel autoclave inside the glovebox. The autoclave was moved out of the glovebox, charged to 20 atm with hydrogen and then closed off to the source of hydrogen. The reaction mixture was heated to 80° C. and stirred at a stirring rate of 700 rpm. At desired reaction time, the reaction was terminated by cooling down and releasing the pressure.

Blank test showed no catalytic activity in the absence of catalysts. The reactants and products were analyzed by a gas chromatograph equipped with an Agilent 19091-413 HP-5 capillary column (30 m×0.32 mm×0.25 μm).

TABLE S1

Hydrogenation of styrene catalysed by as-prepared metal NPs.[a]

| Entry | Catalyst | Time (h) | Conversion (%) | TON[b] (×10³ mol St/mol surface metal) | Selectivity[c] (%) |
|---|---|---|---|---|---|
| 1 | Ni/Al₂O₃ | 0.5 | 63.5 | 3.1 | >99% |
| 2 | | 1.0 | 87.2 | 4.2 | >99% |
| 3 | | 3.0 | 96.5 | 4.7 | >99% |
| 4 | Ni@Pt/Al₂O₃ | 0.5 | 91.7 | 4.4 | >99% |
| 5 | | 1.0 | 93.9 | 4.6 | >99% |
| 6 | | 3.0 | 95.6 | 4.6 | >99% |
| 7 | Ni@Pt@Ni/Al₂O₃ | 0.5 | 77.8 | 3.2 | >99% |
| 8 | | 1.0 | 95.6 | 3.9 | >99% |
| 9 | | 3.0 | 96.6 | 4.0 | >99% |
| 10 | Pt/Al₂O₃ | 0.5 | 85.6 | 5.6 | >99% |
| 11 | | 1.0 | 96.1 | 6.3 | >99% |
| 12 | | 3.0 | 97.9 | 6.4 | >99% |

[a]General reaction conditions: catalyst, 50 mg; $H_2$, 20 atm; 80° C.; toluene, 75 ml; styrene, 4 ml; n-decane as internal standard, 1.4 ml.
[b]The amount of surface metal atoms of NPs was calculated from the formula: $M_s = M_{total} \times D$, where $M_s$ is the amount of surface metal atoms, $M_{total}$ is the amount of the total metal atoms and D is the dispersion of the NPs. D was calculated from the following formula: % D = 97.1/d (assuming in a first approximation that the NPs are spherical, C. H. Bartholomew and R. B. Pannell, J. Catal., 1980, 65, 390-401), where d is the average particle diameter determined by TEM.
[c]selectivity of styrene to ethylbenzene.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to figures and the measurement techniques. In addition, the phrase "about 'x' to 'y'" includes "about 'x' to about 'y'". When a range includes "zero" and is modified by "about" (e.g., about one to zero or about zero to one), about zero can include, 0, 0.1. 0.01, or 0.001.

While only a few embodiments of the present disclosure have been shown and described herein, it will become apparent to those skilled in the art that various modifications and changes can be made in the present disclosure without departing from the spirit and scope of the present disclosure. All such modification and changes coming within the scope of the appended claims are intended to be carried out thereby.

We claim at least the following:

1. A particle, comprising: a supported Ni/Pt bimetallic nanoparticle prepared by a process comprising heating a powder of an $Al_2O_3$-supported crystalline Ni nanoparticle to about 200 to 500° C. under hydrogen flow for about 1 to 5 hours to form a nickel hydride layer on the surface of the Ni nanoparticle ($Ni_s$—H) and mixing the $Al_2O_3$-supported $Ni_s$—H powder with a first solution including $Pt(acac)_2$ for about 10 to 30 hours under hydrogen, wherein the supported Ni/Pt bimetallic nanoparticle has a monolayer of Pt atoms disposed on the surface of the Ni nanoparticle, wherein the supported Ni/Pt bimetallic nanoparticle has a molar ratio of Pt atoms to Ni surface atoms ($Pt/Ni_s$) of 0.1 to 0.94.

2. The particle of claim 1, further comprising a Ni layer disposed on the Pt monolayer and the Ni nanoparticle made by a method comprising mixing the supported Ni/Pt bimetallic nanoparticle with a second solution including $Ni(acac)_2$ for about 10 to 30 hours under hydrogen.

3. The particle of claim 2, wherein the Ni layer has a coverage of about 1 to 100% of the supported Ni/Pt bimetallic nanoparticle.

4. The particle of claim 1, wherein the Ni nanoparticle has a face-centered cubic crystal structure.

5. The particle of claim 4, wherein the {111} and {100} facets of the crystalline Ni nanoparticle are exposed.

6. The particle of claim 1, wherein the Ni/Pt bimetallic nanoparticle has a diameter of about 3 to 15 nm.

7. The particle of claim 1, wherein the molar ratio is 0.94 or the molar ratio is within the range of about 0.6 to 0.8.

8. The particle of claim 1, wherein the support comprising the Ni/Pt bimetallic nanoparticle is free of monometallic Pt or Ni particles.

9. The particle of claim 1, wherein the $Al_2O_3$ is $\gamma$-$Al_3O_2$.

* * * * *